(12) United States Patent
Strohmaier et al.

(10) Patent No.: US 8,025,863 B2
(45) Date of Patent: Sep. 27, 2011

(54) SYNTHESIS AND USE OF MSE-FRAMEWORK TYPE MOLECULAR SIEVES

(75) Inventors: Karl G. Strohmaier, Port Murray, NJ (US); Simon C. Weston, Annandale, NJ (US); James C. Vartuli, West Chester, PA (US); J. Thomas Ippoliti, Woodbury, MN (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 686 days.

(21) Appl. No.: 12/214,631

(22) Filed: Jun. 20, 2008

(65) Prior Publication Data

US 2009/0318696 A1    Dec. 24, 2009

(51) Int. Cl.
*C01B 39/04* (2006.01)
*C01B 39/48* (2006.01)

(52) U.S. Cl. ........................................ 423/706; 423/718
(58) Field of Classification Search ................... 423/706, 423/718
See application file for complete search history.

(56) References Cited

U.S. PATENT DOCUMENTS

| | | | |
|---|---|---|---|
| 3,354,078 A | 11/1967 | Miale et al. | |
| 6,049,018 A | 4/2000 | Calabro et al. | |
| 7,198,711 B1 | 4/2007 | Chester et al. | |

FOREIGN PATENT DOCUMENTS

EP    1852394 A1    11/2007

OTHER PUBLICATIONS

Dorset et al, "Crystal Structure of Zeoite MCM-68: A new Three-Dimensional Framework with Large Pores", J. Phys. Chem. B (110), pp. 2045-2050, (Jan. 2006).*
Angel Cantin, et al., "Synthesis and Structure of the Bidimensional Zeolite ITQ-32 with Small and Large Pores", Journal of the American Chemical Society, 2005, 127, 11560-11561.
Letter to the Editor, "Superactive Crystalline Aluminosilicate Hydrocarbon Catalysts", Journal of Catalysis, 4, 1965, 527-529.
J. N. Miale, et al., Catalysis by Crystalline Aluminosilicates, IV. Attainable Catalytic Cracking Rate Constants, and Superactivity, Journal of Catalysis, 6, 1966, 278-287.
ZSM-5 Substitutional Series, Journal of Catalysis 61, 1980, 395.

* cited by examiner

*Primary Examiner* — David M Brunsman

(57) ABSTRACT

A method of synthesizing a crystalline molecular sieve having an MSE framework type comprises crystallizing a reaction mixture comprising a source of water, a source of an oxide of a tetravalent element, Y, selected from at least one of silicon, tin, titanium, vanadium and germanium, a source of an alkali or alkaline earth metal, M, and a source of organic cations, Q, having the following general structure:

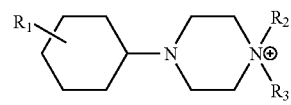

in which $R_1$ is hydrogen or an alkyl group, and $R_2$ and $R_3$ are alkyl groups.

20 Claims, 1 Drawing Sheet

Figure 1: X-ray diffraction pattern of MCM-68 prepared with 1,1-dimethyl-4-cyclohexylpiperazinium

SYNTHESIS AND USE OF MSE-FRAMEWORK TYPE MOLECULAR SIEVES

FIELD

This invention relates to the synthesis of crystalline molecular sieves of the MSE framework-type, such as MCM-68, and to their use in organic conversion processes.

BACKGROUND

MCM-68 is a single crystalline phase molecular sieve material which has a unique 3-dimensional channel structure comprising one 12-membered ring channel system and two 10-membered ring channel systems, in which the channels of each system extend perpendicular to the channels of the other systems and in which the 12-ring channels are generally straight and the 10-ring channels are tortuous (sinusoidal). MCM-68 has been assigned structure type MSE by the Structure Commission of the International Zeolite Association.

The composition and characterizing X-ray diffraction pattern of MCM-68 are disclosed in U.S. Pat. No. 6,049,018, which also describes the synthesis of the molecular sieve in the presence of a structure directing agent comprising the N,N,N',N'-tetraethylbicyclo[2.2.2]oct-7-ene-2,3:5,6-dipyrrolidinium dication. The entire contents of U.S. Pat. No. 6,049,018 are incorporated herein by reference.

U.S. Pat. No. 6,049,018 exemplifies the use of MCM-68 as a catalyst in aromatic alkylation and transalkylation reactions. In addition, U.S. Pat. No. 7,198,711 discloses that MCM-68 shows activity in the catalytic cracking of hydrocarbon feedstocks to produce an enhanced yield of butylenes and isobutene, with the MCM-68 either being the primary cracking catalyst or an additive component in conjunction with a conventional large pore cracking catalyst, such as zeolite Y.

To date, however, the commercial development of MCM-68 has been hindered by the high cost of the dication structure directing agent required for its synthesis and hence there is significant interest in finding alternative, less expensive structure directing agents for the synthesis of MCM-68.

According to the present invention, it has now been found that 1,1-dialkyl-4-cyclohexylpiperazin-1-ium cations and 1,1-dialkyl-4-alkylcyclohexylpiperazin-1-ium cations are effective as structure directing agents in the synthesis of MCM-68. Moreover, it has been found that these cations can be produced conveniently and inexpensively from commercially available raw materials.

European Patent Publication No. EP 1 852 394 A1, published Jul. 11, 2007 and incorporated herein by reference, discloses that the zeolite ITQ-32 can be synthesized in the presence of fluoride ions using 1,1-dimethyl-4-cyclohexylpiperazin-1-ium cations as a structure directing agent. ITQ-32 has a 2-dimensional channel structure comprising 8-membered ring channels and has been assigned structure type IHW by the Structure Commission of the International Zeolite Association. Thus ITQ-32 has a different crystal structure than MCM-68. Moreover, in EP 1 852 394 A1 the 1,1-dimethyl-4-cyclohexylpiperazin-1-ium are produced by alkylation of N-cyclohexylpiperazine with iodomethane, but N-cyclohexylpiperazine is not commercially available and is scarce even at laboratory scale quantities.

SUMMARY

In one aspect, the present invention resides in a method of synthesizing a crystalline molecular sieve having the structure of the MSE framework type, preferably MCM-68, the method comprising crystallizing a reaction mixture comprising a source of water, a source of an oxide of a tetravalent element, Y, selected from at least one of silicon, tin, titanium, vanadium and germanium, optionally a source of a trivalent element, X, a source of an alkali or alkaline earth metal, M, and a source of organic cations, Q, having the following general structure:

in which $R_1$ is hydrogen or an alkyl group, such as a methyl group, and $R_2$ and $R_3$ are alkyl groups and conveniently are independently selected from methyl and ethyl groups.

Conveniently, the molar ratio $Q/YO_2$ in said reaction mixture is in the range of from about 0.01 to about 1.0, such as from about 0.05 to about 0.7.

Conveniently, said reaction mixture comprises a source of an oxide of trivalent element, X, selected from at least one of aluminum, boron, gallium, iron and chromium, conveniently such that molar ratio $YO_2/X_2O_3$ in said reaction mixture is in the range of from about 4 to about 200, such as from about 8 to about 120.

In one embodiment, the reaction mixture has the following molar composition:

| | |
|---|---|
| $YO_2/X_2O_3$ | 4 to 200 |
| $H_2O/YO_2$ | 5 to 200 |
| $OH^-/YO_2$ | 0.05 to 1 |
| $M/YO_2$ | 0.05 to 2 |
| $Q/YO_2$ | 0.01 to 1. |

In another embodiment, the reaction mixture has the following molar composition:

| | |
|---|---|
| $YO_2/X_2O_3$ | 8 to 120 |
| $H_2O/YO_2$ | 14 to 50 |
| $OH^-/YO_2$ | 0.10 to 0.53 |
| $M/YO_2$ | 0.15 to 0.9 |
| $Q/YO_2$ | 0.05 to 0.7. |

Generally, said tetravalent element, Y, is silicon, said trivalent element, X, is aluminum and said alkali or alkaline earth metal, M, is at least one of sodium and potassium.

Conveniently, said reaction mixture comprises seeds of MSE framework type molecular sieve, typically such that the molar ratio of seeds/$YO_2$ in said reaction mixture is between about 0.001 and about 0.1.

Conveniently, the crystallizing is conducted at a temperature between about 100° C. and about 200° C. for up to 28 days, such as at a temperature between about 145° C. and about 175° C. for about 24 to about 170 hours.

In a further aspect, the invention resides in a crystalline molecular sieve having the MSE framework type and containing within its pore structure cations, Q, selected from 1,1-dialkyl-4-cyclohexylpiperazin-1-ium cations, 1,1-dialkyl-4-alkylcyclohexylpiperazin-1-ium cations and mixtures thereof.

In yet a further aspect, the invention resides in an organic conversion process comprising contacting an organic feed with a catalyst comprising a calcined form of the crystalline MSE framework type molecular sieve described herein.

In still yet a further aspect, the invention resides in a process for producing a 1,1-dialkyl-4-cyclohexylpiperazin-1-ium compound, the process comprising:
(a) reacting a halobenzene with 1-alkylpiperazine to produce 1-alkyl-4-phenylpiperazine;
(b) hydrogenating the 1-alkyl-4-phenylpiperazine from (a) to produce 1-alkyl-4-cyclohexylpiperazine; or
(c) reacting 1-alkylpiperazine from (a) with cyclohexanone and hydrogen to produce 1-alkyl-4-cyclohexylpiperazine; and
(d) alkylating the 1-alkyl-4-cyclohexylpiperazine from (b) or (c) to produce a 1,1-dialkyl-4-cyclohexylpiperazin-1-ium compound.

Conveniently, the halobenzene is bromobenzene.

In still yet a further aspect, the invention resides in a process for producing a 1,1-dialkyl-4-alkylcyclohexylpiperazin-1-ium compound, the process comprising:
(a) reacting a haloalkylbenzene with 1-alkylpiperazine to produce 1-alkyl-4-alkylphenylpiperazine;
(b) hydrogenating the 1-alkyl-4-alkylphenylpiperazine from (a) to produce 1-alkyl-4-alkylcyclohexylpiperazine; or
(c) reacting 1-alkylpiperazine from (a) with alkylcyclohexanone and hydrogen to produce 1-alkyl-4-alkylcyclohexylpiperazine; and
(d) alkylating the 1-alkyl-4-alkylcyclohexylpiperazine from (b) or (c) to produce a 1,1-dialkyl-4-alkylcyclohexylpiperazin-1-ium compound.

Conveniently, the haloalkylbenzene is 4-methylbromobenzene.

Conveniently, said alkylating is effected by reacting the 1-alkyl-4-cyclohexylpiperazine or 1-alkyl-4-alkylcyclohexylpiperazine with iodomethane or iodoethane.

DETAILED DESCRIPTION OF THE EMBODIMENTS

Described herein is a method of synthesizing a crystalline molecular sieve having the MSE framework type, such as MCM-68, using 1,1-dialkyl-4-cyclohexylpiperazin-1-ium and/or 1,1-dialkyl-4-alkylcyclohexylpiperazin-1-ium, Q, cations as a structure directing agent, together with an improved method of preparing the structure directing agent. Also described herein is the use of the calcined form of the resultant MSE framework type crystalline molecular sieve as a catalyst in organic conversion reactions, such as in aromatic alkylation and transalkylation reactions and in the catalytic cracking of hydrocarbon feedstocks.

MCM-68 is a synthetic porous single crystalline phase material which has a unique 3-dimensional channel system comprising one 12-membered ring channel system and two 10-membered ring channel systems, in which the channels of each system extend perpendicular to the channels of the other systems and in which the 12-ring channels are generally straight and the 10-ring channels are tortuous (sinusoidal). MCM-68 has been assigned structure type MSE by the Structure Commission of the International Zeolite Association.

In its calcined form, MCM-68 has an X-ray diffraction pattern which is distinguished from the patterns of other known as-synthesized or thermally treated crystalline materials by the lines listed in Table 1 below.

TABLE 1

| d (Å) | Relative Intensity [100 × I/I(o)] |
|---|---|
| 13.60 +/− 0.39 | S |
| 13.00 +/− 0.37 | VS |
| 10.92 +/− 0.31 | M |
| 10.10 +/− 0.29 | M |
| 9.18 +/− 0.26 | VS |
| 8.21 +/− 0.23 | W |
| 4.58 +/− 0.13 | W |
| 4.54 +/− 0.13 | W |
| 4.45 +/− 0.13 | VW-W |
| 4.32 +/− 0.12 | VW |
| 4.22 +/− 0.12 | VW |
| 4.10 +/− 0.12 | VS |
| 4.05 +/− 0.11 | M |
| 3.94 +/− 0.11 | M |
| 3.85 +/− 0.11 | M |
| 3.80 +/− 0.11 | VW |
| 3.40 +/− 0.10 | W |
| 3.24 +/− 0.09 | W |
| 2.90 +/− 0.08 | VW |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units, and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (>80% to ≦100%), s=strong (>60% to ≦80%), m=medium (>40% to ≦60%), w=weak (>20% to ≦40%), and vw=very weak (>0% to ≦20%). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

MCM-68 has a chemical composition involving the molar relationship:

$X_2O_3:(n)YO_2$ wherein X is a trivalent element selected from at least one of aluminum, boron, gallium, iron and chromium, preferably aluminum; Y is a tetravalent element selected from at least one of silicon, tin, titanium, vanadium and germanium, preferably silicon; and n is at least about 4, such as 4 to 100,000, and usually from about 10 to about 100.

MCM-68 is thermally stable and in the calcined form exhibits a high surface area (660 m²/g with micropore volume of 0.21 cc/g) and significant hydrocarbon sorption capacity:

| | |
|---|---|
| n-Hexane sorption at 75 torr, 90° C. | 10.8 wt % |
| Benzene sorption at 75 torr, 30° C. | 18.8 wt % |
| 2,2-Dimethylbutane sorption at 60 torr, 120° C. | 11.0 wt % |
| Mesitylene sorption at 2 torr, 100° C. | 3.3 wt %. |

In its active, hydrogen form MCM-68 exhibits a high acid activity, with an Alpha Value of 900-2000. Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395 (1980).

As disclosed in U.S. Pat. No. 6,049,018, MCM-68 has previously been synthesized using N,N,N',N'-tetraethylbicyclo[2.2.2]oct-7-ene-2,3:5,6-dipyrrolidinium dications as the structure directing agent. However, the high cost of this structure directing agent has significantly hindered the commercial development of MCM-68.

The present method of synthesizing MCM-68 employs as the structure directing agent 1,1-dialkyl-4-cyclohexylpiperazin-1-ium and/or 1,1-dialkyl-4-alkylcyclohexylpiperazin-1-ium cations, which have the following general structure:

in which $R_1$ is hydrogen or an alkyl group, such as a methyl group, and $R_2$ and $R_3$ are alkyl groups and conveniently are independently selected from methyl and ethyl groups. Preferred 1,1-dialkyl-4-alkylcyclohexylpiperazin-1-ium cations are 1,1-dialkyl-4-(4-alkylcyclohexyl)piperazin-1-ium cations.

1,1-dimethyl-4-cyclohexylpiperazin-1-ium cations have previously been used to direct the synthesis of the zeolite ITQ-32 (see European Patent Publication No. EP 1 852 394 A1). However, as with many other structure directing agent systems, it has now been found that, by varying the synthesis conditions, 1,1-dialkyl-4-cyclohexylpiperazin-1-ium cations, including 1,1-dimethyl-4-cyclohexylpiperazin-1-ium cations, are effective in directing the synthesis of a number of different molecular sieve materials, and in particular are effective in directing the synthesis of pure phase MCM-68. Surprisingly, compounds having a similar structure to 1,1-dialkyl-4-cyclohexylpiperazin-1-ium compounds, such as 1,1-diethylbipiperidin-1-ium hydroxide, 1,1-dimethylbipiperidin-1-ium hydroxide, 1,1,4-trimethyl-4-cyclohexylpiperazin-1-ium dihydroxide and 1,1-dimethyl-4-phenylpiperazin-1-ium hydroxide, have so far proved ineffective in directing the synthesis of MCM-68.

In the present method a reaction mixture is produced comprising a source of water, a source of an oxide of a tetravalent element, Y, selected from at least one of silicon, tin, titanium, vanadium and germanium, a source of an oxide of trivalent element, X, selected from at least one of aluminum, boron, gallium, iron and chromium, a source of an alkali or alkaline earth metal, M, together with a source of 1,1-dialkyl-4-cyclohexylpiperazin-1-ium and/or 1,1-dialkyl-4-alkylcyclohexylpiperazin-1-ium, Q, cations. Generally, the composition of the reaction mixture is controlled so that the molar ratio $Q/YO_2$ in said reaction mixture is in the range of from about 0.01 to about 1, such as from about 0.05 to about 0.5. More specifically, the reaction mixture has a composition, in terms of mole ratios of oxides, within the following ranges:

| Reactants | Useful | Preferred |
|---|---|---|
| $YO_2/X_2O_3$ | 4 to 200 | 8 to 120 |
| $H_2O/YO_2$ | 5 to 200 | 14 to 50 |
| $OH^-/YO_2$ | 0.05 to 1 | 0.10 to 0.53 |
| $M/YO_2$ | 0.05 to 2 | 0.15 to 0.9 |
| $Q/YO_2$ | 0.01 to 1 | 0.05 to 0.7 |

Conveniently, the reaction mixture also comprises seeds of MSE framework type molecular sieve, such as MCM-68, typically such that the molar ratio of seeds/$YO_2$ in the reaction mixture is between about 0.001 and about 0.1, such as between about 0.01 and about 0.05.

Generally, the tetravalent element, Y, is silicon, the trivalent element, X, is aluminum and the alkali or alkaline earth metal, M, comprises at least one of sodium and potassium. Typically, the alkali or alkaline earth metal, M, is potassium or potassium and sodium such that the molar ratio of Na to the total metal M is between 0 and about 0.9, preferably between 0 and about 0.5.

Suitable sources of silicon oxide that can be used to produce the reaction mixture described above include colloidal silica, precipitated silica, potassium silicate, sodium silicate, and fumed silica. Similarly, suitable sources of aluminum oxide include hydrated aluminum oxides, such as boehmite, gibbsite, and pseudoboehmite, especially gibbsite, as well as oxygen-containing aluminum salts, such as aluminum nitrate. Suitable sources of alkali metal include sodium and/or potassium hydroxide.

Suitable sources of 1,1-dialkyl-4-cyclohexylpiperazin-1-ium and 1,1-dialkyl-4-alkylcyclohexylpiperazin-1-ium cations include any salts of the substituted piperazine parent compound a which are not detrimental to the formation of the crystalline material MCM-68, for example, the halide, e.g., iodide, or hydroxide.

In this respect, 1,1-dimethyl-4-cyclohexylpiperazin-1-ium iodide is a known compound and is conventionally produced by alkylation of N-cyclohexylpiperazine with iodomethane (EP 1 852 394 A1). However, in view of the scarcity and cost of N-cyclohexylpiperazine, the present invention also resides in a lower cost and industrially more convenient process for the production of 1,1-dialkyl-4-cyclohexylpiperazin-1-ium cations.

In this process, a 1-alkylpiperazine, for example, 1-methylpiperazine, which is commercially available at relatively low cost, is reacted with a halobenzene, typically bromobenzene, at the reflux temperature of the mixture, typically in the presence of a catalyst, such as (1,3-diisopropylimidazol-2-ylidene)(3-chloropyridyl)-palladium(II) dichloride, to produce 1-alkyl-4-phenylpiperazine. The 1-alkyl-4-phenylpiperazine is then hydrogenated, typically in the presence of a catalyst, such as ruthenium on carbon, at a temperature of about 110° C. to about 145° C., under a hydrogen atmosphere at a pressure of about 500 psig to about 800 psig (3550 to 5620 kPa) to produce 1-alkyl-4-cyclohexylpiperazine. 1-alkyl-4-cyclohexylpiperazine may also be prepared by the reaction of 1-alkylpiperazine with cyclohexanone, typically in the presence of a catalyst, such as sulfuric acid, followed by the addition of hydrogen gas, typically in the presence of a catalyst, such as palladium on carbon, at a temperature of about 20° C. to about 75° C. at a pressure of about 14 psig to about 800 psig (200 to 5620 kPa). The 1-alkyl-4-cyclohexylpiperazine is then alkylated, typically by reaction with an alkyl iodide, e.g. iodomethane, at a temperature of about 20° C. to about 80° C., to produce a 1,1-dialkyl-4-cyclohexylpiperazin-1-ium compound.

The same process can be employed to produce the 1,1-dialkyl-4-alkylcyclohexylpiperazin-1-ium cation directing agent, although in this case the 1-alkylpiperazine, for example, 1-methylpiperazine, is reacted with a haloalkylbenzene, typically 4-methylbromobenzene, to produce 1-alkyl-4-alkylphenylpiperazine. The 1-alkyl-4-alkylphenylpiperazine is then hydrogenated to produce 1-alkyl-4-alkylcyclohexylpiperazine, which then alkylated, typically by reaction with an alkyl iodide, e.g. iodomethane, to produce a 1,1-dialkyl-4-alkylcyclohexylpiperazin-1-ium compound.

Irrespective of the source of cations, Q, when the reaction mixture has been prepared, crystallization to produce the desired MCM-68 is conducted under either static or stirred conditions in a suitable reactor vessel, such as for example, polypropylene jars or stainless steel autoclaves optionally lined with Teflon®, at a temperature between about 100° C. and about 200° C. for up to 28 days, such as at a temperature between about 145° C. and about 175° C. for about 24 to about 170 hours. Thereafter, the crystals are separated from the liquid and recovered.

The product of the synthesis reaction is a crystalline molecular sieve having the MSE framework type and containing within its pore structure 1,1-dialkyl-4-cyclohexylpiperazin-1-ium and/or 1,1-dialkyl-4-alkylcyclohexylpiperazin-1-ium cations. The resultant as-synthesized material has an X-ray diffraction pattern which is distinguished from the patterns of other known as-synthesized or thermally treated crystalline materials by the lines listed in Table 2 below.

TABLE 2

| d (Å) | Relative Intensity [100 × I/I(o)] |
|---|---|
| 13.56 +/− 0.39 | VW |
| 12.93 +/− 0.37 | M-S |
| 10.92 +/− 0.31 | W |
| 10.16 +/− 0.29 | VW-W |
| 9.15 +/− 0.26 | VW-W |
| 8.19 +/− 0.23 | VW |
| 4.58 +/− 0.13 | W |
| 4.54 +/− 0.13 | W |
| 4.44 +/− 0.12 | W |
| 4.32 +/− 0.12 | VW |
| 4.23 +/− 0.12 | VW |
| 4.10 +/− 0.12 | VS |
| 4.06 +/− 0.12 | M |
| 3.98 +/− 0.11 | W |
| 3.88 +/− 0.11 | M |
| 3.80 +/− 0.11 | VW |
| 3.40 +/− 0.10 | VW |
| 3.24 +/− 0.09 | W |
| 2.90 +/− 0.08 | VW |

Again, these X-ray diffraction data were collected with a Scintag diffraction system, equipped with a germanium solid state detector, using copper K-alpha radiation and with the diffraction data being recorded by step-scanning at 0.02 degrees of two-theta using a counting time of 10 seconds for each step. As with the Table 1 data, the relative intensities are given in terms of the symbols vs=very strong (>80% to ≦100%), s=strong (>60% to ≦80%), m=medium (>40% to ≦60%), w=weak (>20% to ≦40%), and vw=very weak (>0% to ≦20%).

Since the as-synthesized crystalline molecular sieve contains 1,1-dialkyl-4-cyclohexylpiperazin-1-ium cations and/or 1,1-dialkyl-4-alkylcyclohexylpiperazin-1-ium cations within its pore structure, the product is normally activated before use in such a manner that the organic structure directing agent is removed from the molecular sieve, leaving active catalytic sites within the microporous channels of the molecular sieve open for contact with a feedstock. The activation process is typically accomplished by heating the molecular sieve at a temperature of from about 200° C. to about 800° C. in the presence of an oxygen-containing gas.

To the extent desired, the original sodium and/or potassium cations of the as-synthesized material can be replaced in accordance with techniques well known in the art, at least in part, by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIB, VIIB and VIII of the Periodic Table of the Elements.

The crystalline molecular sieve produced by the present process can be used to catalyze a wide variety of organic compound conversion processes including many of present commercial-industrial importance. Examples of chemical conversion processes which are effectively catalyzed by the crystalline material of this invention, by itself or in combination with one or more other catalytically active substances including other crystalline catalysts, include those requiring a catalyst with acid activity. Specific examples include:

(a) alkylation of aromatics with short chain ($C_2$-$C_6$) olefins, e.g. alkylation of benzene with ethylene or propylene to produce ethylbenzene or cumene respectively, in the gas or liquid phase, with reaction conditions including a temperature of about 10° C. to about 250° C., a pressure of about 0 to 500 psig, a total weight hourly space velocity (WHSV) of about 0.5 $hr^{-1}$ to about 100 $hr^{-1}$, and an aromatic/olefin mole ratio of about 0.1 to about 50;

(b) alkylation of aromatics with long chain ($C_{10}$-$C_{20}$) olefins, in the gas or liquid phase, with reaction conditions including a temperature of about 250° C. to about 500° C., a pressure of about 0 to 500 psig, a total WHSV of about 0.5 $hr^{-1}$ to about 50 $hr^{-1}$, and an aromatic/olefin mole ratio of 1 to about 50;

(c) transalkylation of aromatics, in gas or liquid phase, e.g. transalkylation of polyethylbenzenes or polyisopropylbenzenes with benzene to produce ethylbenzene or cumene respectively, with reaction conditions including a temperature of about 100° C. to about 500° C., a pressure of about 1 to about 500 psig, and a WHSV of about 1 $hr^{-1}$ to about 10,000 $hr^{-1}$;

(d) disproportionation of alkylaromatics, e.g. disproportionation of toluene to produce xylenes, with reaction conditions including a temperature of from about 200° C. to about 760° C., a pressure of from about atmospheric to about 60 atmospheres, a WHSV of about 0.1 $hr^{-1}$ to about 20 $hr^{-1}$, and a hydrogen/hydrocarbon mole ratio of 0 (no added hydrogen) to about 50;

(e) dealkylation of alkylaromatics, e.g. deethylation of ethylbenzene, with reaction conditions including a temperature of from about 200° C. to about 760° C., a pressure of from about atmospheric to about 60 atmospheres, a WHSV of about 0.1 hr$^{-1}$ to about 20 hr$^{-1}$, and a hydrogen/hydrocarbon mole ratio of 0 (no added hydrogen) to about 50;

(f) isomerization of alkylaromatics, such as xylenes, with reaction conditions including a temperature of from about 200° C. to about 540° C., a pressure of from about 100 to about 7000 kPa, a WHSV of about 0.1 hr$^{-1}$ to about 50 hr$^{-1}$, and a hydrogen/hydrocarbon mole ratio of 0 (no added hydrogen) to about 10;

(g) reaction of paraffins with aromatics to form alkylaromatics and light gases with reaction conditions including a temperature of about 260° C. to about 375° C., a pressure of about 0 to about 1000 psig, a WHSV of about 0.5 hr$^{-1}$ to about 10 hr$^{-1}$, and a hydrogen/hydrocarbon mole ratio of 0 (no added hydrogen) to about 10;

(h) paraffin isomerization to provide branched paraffins with reaction conditions including a temperature of about 200° C. to about 315° C., a pressure of about 100 to 1000 psig, a WHSV of about 0.5 hr$^{-1}$ to about 10 hr$^{-1}$, and a hydrogen/hydrocarbon mole ratio of about 0.5 to about 10;

(i) alkylation of iso-paraffins, such as isobutane, with olefins, with reaction conditions including a temperature of about −20° C. to about 350° C., a pressure of 0 to 700 psig, a total olefin WHSV of about 0.02 hr$^{-1}$ to about 10 hr$^{-1}$;

(j) dewaxing of paraffinic feeds with reaction conditions including a temperature of from about 200° C. to about 450° C., a pressure of about 0 to 1000 psig, a WHSV of about 0.2 hr$^{-1}$ to about 10 hr$^{-1}$, and a hydrogen/hydrocarbon mole ratio of about 0.5 to about 10;

(k) cracking of hydrocarbons with reaction conditions including a temperature of about 300° C. to about 700° C., a pressure of about 0.1 to about 30 atmospheres, and a WHSV of about 0.1 hr$^{-1}$ to about 20 hr$^{-1}$; and (l) isomerization of olefins with reaction conditions including a temperature of about 250° C. to about 750° C., an olefin partial pressure of about 30 to about 300 kPa, and a WHSV of about 0.5 hr$^{-1}$ to about 500 hr$^{-1}$.

As in the case of many catalysts, it may be desirable to incorporate the molecular sieve produced by the present process with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the molecular sieve produced by the present process, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the molecular sieve produced by the present process include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the molecular sieve produced by the present process also include inorganic oxides, such as silica, zirconia, titania, magnesia, beryllia, alumina, and mixtures thereof.

In addition to the foregoing materials, the molecular sieve produced by the present process can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline molecular sieve material and inorganic oxide matrix vary widely, with the crystal content ranging from about 1 to about 90 percent by weight and more usually, particularly when the composite is prepared in the form of beads or extrudates, in the range of about 2 to about 80 weight percent of the composite.

In order to more fully illustrate the nature of the invention and the manner of practicing same, the following examples are presented.

Example 1

Production of 1-methyl-4-phenylpiperazine

A 1 L flask was charged with 141.3 g of bromobenzene, 30.1 g of 1-methylpiperazine and 43.8 g of potassium tert-butoxide. The flask was then placed on an ice bath for 10 minutes and the contents rapidly stirred. 2.04 g of "PEPPSI" catalyst[1,3-bis(2,6-diisopropylphenyl)imidazol-2-ylidene] (3-chloropyridyl)-palladium (II) dichloride was then added and the flask fitted with a reflux condenser. The reaction was refluxed under a nitrogen atmosphere for 2 hours and then cooled to room temperature. The reaction mixture was then filtered through a pad of 800 mL of silica gel in a 2 L D-filter flask and the pad subsequently rinsed with 600 mL of ether. Then the product was extracted from the pad with ethanol. Evaporation of the ethanol gave 39.4 g of 1-methyl-4-phenylpiperazine.

Example 2

Production of 1-methyl-4-cyclohexylpiperazine

A 500 mL steel bomb hydrogenator was charged with 38 g of 1-methyl-4-phenylpiperazine, 200 mL of degassed ethanol, and 4 g of a ruthenium 5% on carbon catalyst. The flask was evacuated and purged with hydrogen gas twice, the second time leaving the flask at 800 psig (5620 kPa). The reaction mixture was then heated to 120° C. and left overnight. The next morning the pressure in the flask had decreased significantly; the reaction was cooled, re-pressurized and again brought up to temperature. This was repeated until a minimal pressure decrease was noticed. The reaction mixture was then passed through a thin pad of celite producing a liquid that was subsequently distilled to give 37 g of 1-methyl-4-cyclohexylpiperazine.

Example 3

Production of 1-methyl-4-cyclohexylpiperazine

A 100 mL flask was charged with 3.02 g of cyclohexanone, 3.19 g of 1-methylpiperazine, 25 mL of ethanol, 3 drops of concentrated sulfuric acid and a catalytic amount of Pd/C, typically 5 mol %. A balloon filled with hydrogen gas was attached. After stirring for 4 days the reaction mixture was filtered through Celite and concentrated to give 2.91 g of 1-methyl-4-cyclohexylpiperazine.

Example 4

Production of 1-methyl-4-cyclohexylpiperazine

A 100 mL flask was charged with 7.36 g of cyclohexanone, 7.81 g of 1-methylpiperazine, 100 mL of anhydrous ethanol and 3 drops of concentrated sulfuric acid. After refluxing for 30 minutes the reaction mixture was cooled and stirred at room temperature overnight. Then a catalytic amount of Pd/C, typically 5 mol % was added and a balloon filled with hydrogen gas was attached. After stirring for 2 days the reaction mixture was filtered through Celite and concentrated to give 1-methyl-4-cyclohexylpiperazine.

Example 5

Production of 1,1-dimethyl-4-cyclohexylpiperazin-1-ium iodide

A 50 mL flask was charged with 1.02 g of 1-methyl-4-cyclohexylpiperazine, 20 mL of anhydrous ethanol, and 0.88 g of iodomethane. After 3 days of stirring under a nitrogen atmosphere the solution was placed into a new flask and quenched with 200 mL ether producing a white crystalline solid. The solid was filtered and rinsed with additional ether and then dried in a vacuum oven overnight at 30° C. and −25 bar to give 1.74 g of 1,1-dimethyl-4-cyclohexylpiperazin-1-ium iodide.

Example 6

Production of 1,1-dimethyl-4-cyclohexylpiperazin-1-ium hydroxide

A column was charged with 116 g of MTO-DOWEX SBR LCNG(OH) resin, and 43.73 g of 1,1-dimethyl-4-cyclohexylpiperazin-1-ium iodide. Distilled water was eluted through the column until the pH was 10 and the resulting solution concentrated to give 100 mL of a 27.7 wt. % solution of 1,1-dimethyl-4-cyclohexylpiperazin-1-ium hydroxide.

Example 7

Synthesis of MCM-68

Figure 1:
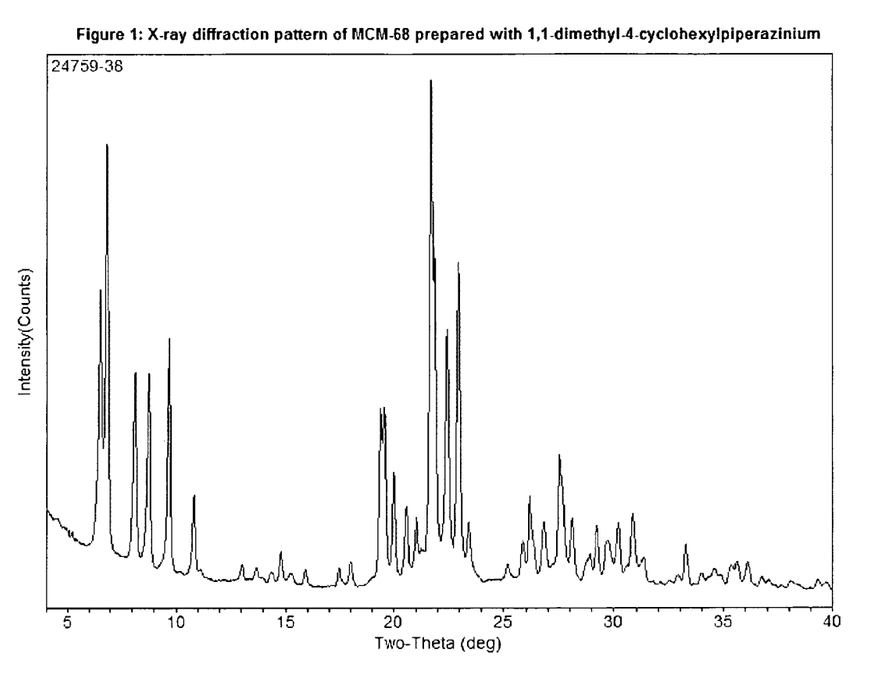
FIG. 1 is an X-ray diffraction pattern of MCM-68 produced using 1,1-dimethyl-4-cyclohexylpiperazin-1-ium cations as the structure directing agent according to the process of Example 2.

A gel of stoichiometry:

6SDA-OH:6KNO$_3$:Al$_2$O$_3$:19.3SiO$_2$:554H$_2$O where SDA-OH is 1,1-dimethyl-4-cyclohexylpiperazin-1-ium hydroxide produced as in Example 6, was prepared by mixing together 16.6 g of DuPont Ludox LS-30 (30.1 wt. % SiO$_2$), 21.1 g of a 27.7 wt. % aqueous solution of 1,1-dimethyl-4-cyclohexylpiperazin-1-ium hydroxide, and 8.7 g of 17.5 wt. % solution of potassium hydroxide. The mixture was stirred with a spatula until homogenous. Then 12.9 g of a 15 wt. % solution of aluminum nitrate, 0.4 g of deionized water and 0.29 g of MCM-68 seeds were added. The mixture was again stirred with a spatula and then thoroughly homogenized in a 100 ml stainless steel laboratory blender. The mixture was transferred to a 125 ml Teflon lined autoclave and reacted at 200° C. for 4 days in a tumbling (30 rpm) oven. The product was recovered by filtration, washed thoroughly with deionized water and then dried at 115° C. in an oven. Phase analysis by powder X-ray diffraction (FIG. 1) showed the sample to be pure MCM-68. Elemental analysis by ICP-AES (Inductively Coupled Plasma—Atomic Emmission Spectroscopy) after dissolution in aqueous HF solution gave 32.34% Si, 3.57% Al, 0.055% Na, and 2.47% K, and thermogravimetric analysis showed a 12.7% organic weight loss which represents a product stoichiometry of:

5.5 K, 0.2 Na, 5.6 SDA-OH[Al$_{11.5}$, Si$_{100.5}$]O$_{224}$

Example 8

Synthesis of MCM-68

A gel was prepared by adding 8.6 mg deionized water, 154.7 mg Kasil-1 potassium silicate solution (8.3% K$_2$O, 20.8% SiO$_2$), 14.3 mg 17.54% KOH solution, 105.8 mg 3.0% NaOH solution, 154.5 mg 35.6% 1,1-dimethyl-4-cyclohexylpiperazin-1-ium iodide solution, 60.4 mg 20% Al(NO$_3$)$_3$ solution and 1.8 mg MCM-68 seeds to a 1.5 ml stainless steel autoclave. The starting gel had the following molar ratios

| | |
|---|---|
| Si/Al | 10 |
| OH$^-$/Si | 0.4 |
| SDA/Si | 0.3 |
| Alkali metal/Si | 0.7 |
| Na/Total Alkali metal | 0.2 |
| Water/Si | 37 |
| Si from Seeds/Total silica | 0.05 | where SDA is the 1,1-dimethyl-4-cyclohexylpiperazin-1-ium structure directing agent. The mixture was stirred until homogenous and then reacted at autogenous pressure at 145° C. for 7 days in an air oven with tumbling. The product was centrifuged, washed three times with deionized water and then subjected to powder X-ray diffraction analysis. The X-ray diffraction pattern showed the product to be pure MCM-68 zeolite.

Example 9

Synthesis of MCM-68

A gel was prepared by adding 8.7 mg deionized water, 42.0 mg UltraSil precipitated silica (92.7% SiO$_2$), 235.3 mg 21.9% 1,1-dimethyl-4-cyclohexylpiperazin-1-ium hydroxide solution, 52.7 mg 17.54% KOH solution, 54.9 mg 3.0% NaOH solution, 31.1 mg 35.6% 1,1-dimethyl-4-cyclohexylpiperazin-1-ium iodide solution, 73.0 mg 20% Al(NO$_3$)$_3$ solution and 2.3 mg MCM-68 seeds to a 1.5 ml stainless steel autoclave. The starting gel had the following molar ratios:

| | |
|---|---|
| Si/Al | 10 |
| OH$^-$/Si | 0.35 |
| SDA/Si | 0.4 |
| Alkali metal/Si | 0.3 |
| Na/Total Alkali metal | 0.2 |
| Water/Si | 30 |
| Si from Seeds/Total silica | 0.05 |

The mixture was stirred until homogenous and then reacted at autogenous pressure at 145° C. for 7 days in an air oven with tumbling. The product was centrifuged, washed three times with deionized water and then subjected to powder X-ray diffraction analysis. The X-ray diffraction pattern showed the product to be pure MCM-68 zeolite.

Example 10

Synthesis of MCM-68

A gel was prepared by adding 0.9 mg deionized water, 160.4 mg Ludox LS-30 (30% $SiO_2$), 140.8 mg 17.54% KOH solution, 123.0 mg 35.6% 1,1-dimethyl-4-cyclohexylpiperazin-1-ium iodide solution, 72.1 mg 20% $Al(NO_3)_3$ solution and 2.7 mg MCM-68 seeds to a 1.5 ml stainless steel autoclave. The starting gel had the following molar ratios:

| | |
|---|---|
| Si/Al | 12.5 |
| $OH^-$/Si | 0.28 |
| SDA/Si | 0.4 |
| Alkali metal/Si | 0.52 |

-continued

| | |
|---|---|
| Na/Total Alkali metal | 0.0 |
| Water/Si | 24 |
| Si from Seeds/Total silica | 0.05 |

The mixture was stirred until homogenous and then reacted at autogenous pressure at 145° C. for 7 days in an air oven with tumbling. The product was centrifuged, washed three times with deionized water and then subjected to powder X-ray diffraction analysis. The X-ray diffraction pattern showed the product to be pure MCM-68 zeolite.

Example 11 to 180

Further MCM-68 Syntheses

A series of gels were prepared in a manner similar to Examples 8 to 10 above, but having the molar ratios indicated below and reacted at the temperature and time indicated. In each case the target Si from Seeds/Total silica ratio was 0.05. In addition, M designates total alkali metal (that is potassium plus any sodium).

| Ex. | Si Source | Si/Al | M/Si | Na/M | OH—/Si | SDA/Si | $H_2O$/Si | Temp ° C. | Time days |
|---|---|---|---|---|---|---|---|---|---|
| 11 | Kasil-1 | 10 | 0.65 | 0.1 | 0.35 | 0.20 | 28 | 145 | 7 |
| 12 | Kasil-1 | 10 | 0.53 | 0.1 | 0.30 | 0.20 | 27 | 145 | 7 |
| 13 | UltraSil | 12.5 | 0.52 | 0.2 | 0.28 | 0.16 | 23 | 145 | 7 |
| 14 | Kasil-1 | 12.5 | 0.54 | 0.1 | 0.32 | 0.32 | 29 | 145 | 7 |
| 15 | Kasil-1 | 7.5 | 0.48 | 0 | 0.47 | 0.40 | 34 | 145 | 7 |
| 16 | Kasil-1 | 10 | 0.60 | 0.2 | 0.30 | 0.40 | 37 | 145 | 7 |
| 17 | Ludox | 12.5 | 0.56 | 0.1 | 0.32 | 0.16 | 28 | 145 | 7 |
| 18 | Ludox | 10 | 0.60 | 0.2 | 0.30 | 0.20 | 35 | 145 | 7 |
| 19 | Ludox | 12.5 | 0.52 | 0 | 0.28 | 0.32 | 30 | 145 | 7 |
| 20 | Ludox | 10 | 0.55 | 0.1 | 0.25 | 0.20 | 30 | 145 | 7 |
| 21 | Kasil-1 | 10 | 0.53 | 0.1 | 0.25 | 0.20 | 26 | 145 | 7 |
| 22 | Kasil-1 | 10 | 0.60 | 0.2 | 0.30 | 0.30 | 34 | 145 | 7 |
| 23 | Ludox | 10 | 0.40 | 0 | 0.35 | 0.30 | 31 | 145 | 7 |
| 24 | Ludox | 10 | 0.70 | 0.2 | 0.40 | 0.20 | 37 | 145 | 7 |
| 25 | Kasil-1 | 7.5 | 0.48 | 0 | 0.40 | 0.40 | 33 | 175 | 3 |
| 26 | Ludox | 12.5 | 0.56 | 0.2 | 0.32 | 0.16 | 31 | 145 | 7 |
| 27 | Kasil-1 | 10 | 0.48 | 0 | 0.30 | 0.20 | 23 | 160 | 3 |
| 28 | Ludox | 15 | 0.37 | 0 | 0.17 | 0.20 | 23 | 160 | 3 |
| 29 | Kasil-1 | 12.5 | 0.48 | 0 | 0.20 | 0.16 | 21 | 160 | 3 |
| 30 | Kasil-1 | 12.5 | 0.54 | 0.1 | 0.32 | 0.16 | 24 | 160 | 3 |
| 31 | Ludox | 12.5 | 0.52 | 0.1 | 0.28 | 0.24 | 30 | 160 | 3 |
| 32 | UltraSil | 10 | 0.60 | 0.2 | 0.30 | 0.20 | 28 | 160 | 3 |
| 33 | UltraSil | 12.5 | 0.56 | 0.1 | 0.32 | 0.24 | 24 | 160 | 3 |
| 34 | Ludox | 10 | 0.65 | 0.1 | 0.35 | 0.30 | 36 | 160 | 3 |
| 35 | Kasil-1 | 12.5 | 0.60 | 0.2 | 0.32 | 0.32 | 35 | 160 | 3 |
| 36 | Kasil-1 | 12.5 | 0.54 | 0.1 | 0.32 | 0.16 | 24 | 160 | 3 |
| 37 | UltraSil | 15 | 0.27 | 0 | 0.17 | 0.27 | 17 | 160 | 3 |
| 38 | Kasil-1 | 10 | 0.53 | 0.1 | 0.40 | 0.20 | 28 | 160 | 3 |
| 39 | Kasil-1 | 12.5 | 0.60 | 0.2 | 0.32 | 0.32 | 35 | 160 | 3 |
| 40 | Kasil-1 | 15 | 0.48 | 0 | 0.23 | 0.20 | 22 | 160 | 3 |
| 41 | Kasil-1 | 12.5 | 0.48 | 0 | 0.28 | 0.24 | 23 | 160 | 3 |
| 42 | Kasil-1 | 10 | 0.53 | 0.1 | 0.20 | 0.40 | 34 | 160 | 3 |
| 43 | Ludox | 7.5 | 0.40 | 0 | 0.47 | 0.53 | 42 | 160 | 3 |
| 44 | UltraSil | 15 | 0.43 | 0 | 0.23 | 0.20 | 17 | 160 | 3 |
| 45 | Kasil-1 | 15 | 0.60 | 0.2 | 0.27 | 0.13 | 30 | 160 | 3 |
| 46 | Kasil-1 | 10 | 0.60 | 0.2 | 0.30 | 0.40 | 37 | 160 | 3 |
| 47 | UltraSil | 10 | 0.70 | 0.1 | 0.40 | 0.20 | 26 | 160 | 3 |
| 48 | UltraSil | 7.5 | 0.40 | 0.2 | 0.33 | 0.40 | 34 | 175 | 3 |
| 49 | Kasil-1 | 10 | 0.60 | 0.2 | 0.40 | 0.40 | 38 | 160 | 3 |
| 50 | Kasil-1 | 10 | 0.53 | 0.1 | 0.30 | 0.40 | 33 | 160 | 3 |
| 51 | Kasil-1 | 12.5 | 0.60 | 0.2 | 0.24 | 0.32 | 36 | 160 | 3 |
| 52 | Kasil-1 | 10 | 0.60 | 0.1 | 0.30 | 0.20 | 27 | 160 | 7 |
| 53 | Kasil-1 | 15 | 0.54 | 0.1 | 0.20 | 0.20 | 27 | 160 | 7 |
| 54 | Kasil-1 | 12.5 | 0.54 | 0.1 | 0.32 | 0.32 | 29 | 160 | 7 |
| 55 | Kasil-1 | 12.5 | 0.54 | 0.1 | 0.24 | 0.32 | 30 | 160 | 7 |
| 56 | Kasil-1 | 15 | 0.60 | 0.2 | 0.27 | 0.13 | 30 | 160 | 7 |
| 57 | Kasil-1 | 10 | 0.53 | 0.1 | 0.20 | 0.30 | 31 | 160 | 7 |
| 58 | UltraSil | 12.5 | 0.32 | 0.2 | 0.32 | 0.32 | 26 | 160 | 7 |

-continued

| Ex. | Si Source | Si/Al | M/Si | Na/M | OH—/Si | SDA/Si | $H_2O$/Si | Temp °C. | Time days |
|---|---|---|---|---|---|---|---|---|---|
| 59 | Kasil-1 | 7.5 | 0.48 | 0 | 0.47 | 0.53 | 38 | 160 | 7 |
| 60 | Kasil-1 | 10 | 0.60 | 0.2 | 0.20 | 0.40 | 39 | 160 | 7 |
| 61 | Kasil-1 | 12.5 | 0.48 | 0 | 0.24 | 0.24 | 23 | 160 | 7 |
| 62 | UltraSil | 10 | 0.70 | 0.2 | 0.40 | 0.30 | 33 | 160 | 7 |
| 63 | Kasil-1 | 15 | 0.48 | 0 | 0.27 | 0.20 | 21 | 160 | 7 |
| 64 | Kasil-1 | 7.5 | 0.48 | 0 | 0.33 | 0.27 | 28 | 175 | 3 |
| 65 | UltraSil | 12.5 | 0.48 | 0.1 | 0.24 | 0.24 | 22 | 160 | 7 |
| 66 | Kasil-1 | 7.5 | 0.48 | 0 | 0.33 | 0.40 | 33 | 175 | 3 |
| 67 | UltraSil | 15 | 0.43 | 0.2 | 0.23 | 0.13 | 20 | 160 | 7 |
| 68 | Kasil-1 | 15 | 0.48 | 0 | 0.23 | 0.27 | 24 | 160 | 7 |
| 69 | Kasil-1 | 10 | 0.48 | 0 | 0.20 | 0.30 | 26 | 160 | 7 |
| 70 | Kasil-1 | 12.5 | 0.60 | 0.2 | 0.32 | 0.24 | 33 | 160 | 7 |
| 71 | Kasil-1 | 7.5 | 0.53 | 0.1 | 0.40 | 0.53 | 41 | 175 | 3 |
| 72 | Kasil-1 | 15 | 0.54 | 0.1 | 0.27 | 0.13 | 24 | 160 | 7 |
| 73 | Ludox | 15 | 0.37 | 0 | 0.17 | 0.13 | 21 | 160 | 7 |
| 74 | Ludox | 7.5 | 0.53 | 0 | 0.33 | 0.40 | 37 | 160 | 7 |
| 75 | Kasil-1 | 12.5 | 0.54 | 0.1 | 0.24 | 0.32 | 30 | 160 | 7 |
| 76 | UltraSil | 10 | 0.40 | 0.2 | 0.40 | 0.40 | 32 | 160 | 7 |
| 77 | Kasil-1 | 7.5 | 0.60 | 0.2 | 0.33 | 0.53 | 45 | 145 | 7 |
| 78 | UltraSil | 12.5 | 0.56 | 0.1 | 0.32 | 0.16 | 21 | 160 | 7 |
| 79 | Kasil-1 | 7.5 | 0.60 | 0.2 | 0.33 | 0.53 | 45 | 175 | 3 |
| 80 | Kasil-1 | 15 | 0.48 | 0 | 0.17 | 0.13 | 21 | 160 | 7 |
| 81 | Ludox | 12.5 | 0.56 | 0.1 | 0.32 | 0.24 | 31 | 175 | 3 |
| 82 | Kasil-1 | 15 | 0.60 | 0.2 | 0.27 | 0.20 | 32 | 175 | 3 |
| 83 | Kasil-1 | 7.5 | 0.53 | 0.1 | 0.47 | 0.40 | 37 | 175 | 3 |
| 84 | UltraSil | 7.5 | 0.87 | 0.2 | 0.47 | 0.40 | 43 | 175 | 3 |
| 85 | Ludox | 7.5 | 0.40 | 0.2 | 0.53 | 0.53 | 47 | 175 | 3 |
| 86 | UltraSil | 10 | 0.55 | 0 | 0.25 | 0.30 | 23 | 175 | 3 |
| 87 | Kasil-1 | 12.5 | 0.60 | 0.2 | 0.28 | 0.32 | 35 | 175 | 3 |
| 88 | UltraSil | 12.5 | 0.40 | 0 | 0.16 | 0.16 | 16 | 175 | 3 |
| 89 | Kasil-1 | 15 | 0.48 | 0 | 0.20 | 0.27 | 24 | 175 | 3 |
| 90 | UltraSil | 7.5 | 0.53 | 0.1 | 0.53 | 0.40 | 35 | 175 | 3 |
| 91 | Kasil-1 | 7.5 | 0.60 | 0.2 | 0.47 | 0.40 | 42 | 175 | 3 |
| 92 | Ludox | 12.5 | 0.44 | 0 | 0.20 | 0.16 | 23 | 175 | 3 |
| 93 | Ludox | 7.5 | 0.73 | 0.2 | 0.33 | 0.40 | 46 | 160 | 7 |
| 94 | Ludox | 10 | 0.60 | 0 | 0.30 | 0.20 | 28 | 175 | 3 |
| 95 | Ludox | 10 | 0.55 | 0.1 | 0.25 | 0.20 | 30 | 175 | 3 |
| 96 | UltraSil | 15 | 0.37 | 0 | 0.17 | 0.13 | 14 | 175 | 3 |
| 97 | Kasil-1 | 7.5 | 0.60 | 0.2 | 0.47 | 0.27 | 37 | 175 | 3 |
| 98 | Kasil-1 | 15 | 0.54 | 0.1 | 0.23 | 0.20 | 26 | 175 | 3 |
| 99 | Kasil-1 | 7.5 | 0.60 | 0.2 | 0.27 | 0.27 | 35 | 160 | 7 |
| 100 | UltraSil | 15 | 0.20 | 0 | 0.13 | 0.20 | 15 | 175 | 3 |
| 101 | Kasil-1 | 10 | 0.48 | 0 | 0.35 | 0.40 | 30 | 175 | 3 |
| 102 | Kasil-1 | 7.5 | 0.60 | 0.2 | 0.27 | 0.27 | 35 | 175 | 3 |
| 103 | Kasil-1 | 7.5 | 0.60 | 0.2 | 0.27 | 0.53 | 44 | 160 | 7 |
| 104 | Kasil-1 | 7.5 | 0.60 | 0.2 | 0.47 | 0.53 | 46 | 175 | 3 |
| 105 | Kasil-1 | 15 | 0.54 | 0.1 | 0.27 | 0.20 | 26 | 175 | 3 |
| 106 | Ludox | 10 | 0.65 | 0.1 | 0.35 | 0.30 | 36 | 175 | 3 |
| 107 | Kasil-1 | 7.5 | 0.60 | 0.2 | 0.27 | 0.53 | 44 | 175 | 3 |
| 108 | Ludox | 7.5 | 0.67 | 0 | 0.27 | 0.27 | 33 | 160 | 7 |
| 109 | Ludox | 15 | 0.47 | 0.1 | 0.27 | 0.13 | 25 | 175 | 3 |
| 110 | Kasil-1 | 12.5 | 0.48 | 0 | 0.24 | 0.24 | 23 | 175 | 3 |
| 111 | Kasil-1 | 10 | 0.48 | 0 | 0.35 | 0.20 | 24 | 175 | 3 |
| 112 | Kasil-1 | 12.5 | 0.60 | 0.2 | 0.32 | 0.32 | 35 | 175 | 3 |
| 113 | UltraSil | 7.5 | 0.67 | 0.2 | 0.27 | 0.27 | 33 | 175 | 3 |
| 114 | Kasil-1 | 7.5 | 0.60 | 0.2 | 0.53 | 0.53 | 47 | 175 | 3 |
| 115 | Kasil-1 | 10 | 0.60 | 0 | 0.30 | 0.15 | 25 | 160 | 3 |
| 116 | Kasil-1 | 10 | 0.55 | 0 | 0.25 | 0.10 | 20 | 160 | 3 |
| 117 | Kasil-1 | 10 | 0.65 | 0 | 0.35 | 0.08 | 25 | 160 | 3 |
| 118 | Kasil-1 | 10 | 0.55 | 0 | 0.25 | 0.10 | 20 | 160 | 7 |
| 119 | Kasil-1 | 10 | 0.60 | 0 | 0.30 | 0.10 | 25 | 160 | 7 |
| 120 | Kasil-1 | 10 | 0.55 | 0 | 0.25 | 0.05 | 20 | 160 | 7 |
| 121 | Kasil-1 | 10 | 0.50 | 0 | 0.20 | 0.03 | 20 | 160 | 7 |
| 122 | UltraSil | 10 | 0.65 | 0 | 0.35 | 0.20 | 25 | 160 | 3 |
| 123 | UltraSil | 10 | 0.55 | 0 | 0.25 | 0.15 | 20 | 160 | 3 |
| 124 | UltraSil | 10 | 0.55 | 0 | 0.25 | 0.10 | 20 | 160 | 3 |
| 125 | UltraSil | 10 | 0.60 | 0 | 0.30 | 0.10 | 20 | 160 | 3 |
| 126 | UltraSil | 10 | 0.55 | 0 | 0.25 | 0.08 | 20 | 160 | 3 |
| 127 | UltraSil | 10 | 0.60 | 0 | 0.30 | 0.08 | 20 | 160 | 3 |
| 128 | UltraSil | 10 | 0.55 | 0 | 0.25 | 0.05 | 20 | 160 | 3 |
| 129 | UltraSil | 10 | 0.60 | 0 | 0.30 | 0.20 | 25 | 160 | 3 |
| 130 | UltraSil | 10 | 0.65 | 0 | 0.35 | 0.25 | 25 | 160 | 3 |
| 131 | UltraSil | 10 | 0.55 | 0 | 0.25 | 0.15 | 20 | 160 | 3 |
| 132 | UltraSil | 10 | 0.60 | 0 | 0.30 | 0.15 | 20 | 160 | 3 |
| 133 | UltraSil | 10 | 0.55 | 0 | 0.25 | 0.10 | 20 | 160 | 3 |
| 134 | UltraSil | 10 | 0.60 | 0 | 0.30 | 0.10 | 20 | 160 | 3 |
| 135 | UltraSil | 10 | 0.65 | 0 | 0.35 | 0.10 | 20 | 160 | 3 |

-continued

| Ex. | Si Source | Si/Al | M/Si | Na/M | OH—/Si | SDA/Si | $H_2O$/Si | Temp °C. | Time days |
|---|---|---|---|---|---|---|---|---|---|
| 136 | UltraSil | 10 | 0.60 | 0 | 0.30 | 0.08 | 20 | 160 | 3 |
| 137 | UltraSil | 10 | 0.65 | 0 | 0.35 | 0.08 | 20 | 160 | 3 |
| 138 | Kasil-1 | 20 | 0.48 | 0 | 0.25 | 0.20 | 25 | 160 | 3 |
| 139 | Kasil-1 | 20 | 0.48 | 0 | 0.30 | 0.20 | 25 | 160 | 3 |
| 140 | Kasil-1 | 20 | 0.48 | 0 | 0.25 | 0.10 | 20 | 160 | 3 |
| 141 | Kasil-1 | 25 | 0.48 | 0 | 0.25 | 0.20 | 25 | 160 | 3 |
| 142 | Kasil-1 | 25 | 0.48 | 0 | 0.25 | 0.10 | 20 | 160 | 3 |
| 143 | Kasil-1 | 30 | 0.48 | 0 | 0.25 | 0.20 | 25 | 160 | 3 |
| 144 | Kasil-1 | 35 | 0.48 | 0 | 0.30 | 0.10 | 20 | 160 | 3 |
| 145 | Kasil-1 | 20 | 0.48 | 0 | 0.25 | 0.20 | 25 | 160 | 7 |
| 146 | Kasil-1 | 20 | 0.48 | 0 | 0.30 | 0.20 | 25 | 160 | 7 |
| 147 | Kasil-1 | 20 | 0.48 | 0 | 0.25 | 0.10 | 20 | 160 | 7 |
| 148 | Kasil-1 | 20 | 0.48 | 0 | 0.30 | 0.10 | 20 | 160 | 7 |
| 149 | Kasil-1 | 25 | 0.48 | 0 | 0.25 | 0.20 | 25 | 160 | 7 |
| 150 | Kasil-1 | 25 | 0.48 | 0 | 0.25 | 0.10 | 20 | 160 | 7 |
| 151 | Kasil-1 | 25 | 0.48 | 0 | 0.30 | 0.10 | 20 | 160 | 7 |
| 152 | Kasil-1 | 40 | 0.48 | 0 | 0.25 | 0.20 | 25 | 160 | 7 |
| 153 | UltraSil | 20 | 0.40 | 0 | 0.25 | 0.20 | 20 | 160 | 3 |
| 154 | UltraSil | 20 | 0.45 | 0 | 0.30 | 0.20 | 20 | 160 | 3 |
| 155 | UltraSil | 20 | 0.40 | 0 | 0.25 | 0.10 | 20 | 160 | 3 |
| 156 | UltraSil | 20 | 0.45 | 0 | 0.30 | 0.10 | 20 | 160 | 3 |
| 157 | UltraSil | 25 | 0.37 | 0 | 0.25 | 0.20 | 20 | 160 | 3 |
| 158 | UltraSil | 25 | 0.37 | 0 | 0.25 | 0.10 | 20 | 160 | 3 |
| 159 | UltraSil | 25 | 0.42 | 0 | 0.30 | 0.10 | 20 | 160 | 3 |
| 160 | UltraSil | 30 | 0.35 | 0 | 0.25 | 0.20 | 20 | 160 | 3 |
| 161 | UltraSil | 30 | 0.35 | 0 | 0.25 | 0.10 | 20 | 160 | 3 |
| 162 | UltraSil | 30 | 0.40 | 0 | 0.30 | 0.10 | 20 | 160 | 3 |
| 163 | UltraSil | 35 | 0.34 | 0 | 0.25 | 0.10 | 20 | 160 | 3 |
| 164 | UltraSil | 35 | 0.39 | 0 | 0.30 | 0.10 | 20 | 160 | 3 |
| 165 | UltraSil | 40 | 0.33 | 0 | 0.25 | 0.10 | 20 | 160 | 3 |
| 166 | UltraSil | 50 | 0.36 | 0 | 0.30 | 0.10 | 20 | 160 | 3 |
| 167 | UltraSil | 20 | 0.40 | 0 | 0.25 | 0.20 | 20 | 160 | 7 |
| 168 | UltraSil | 20 | 0.45 | 0 | 0.30 | 0.10 | 20 | 160 | 7 |
| 169 | UltraSil | 25 | 0.37 | 0 | 0.25 | 0.10 | 20 | 160 | 7 |
| 170 | Kasil-1 | 10 | 0.60 | 0 | 0.30 | 0.15 | 25 | 160 | 2 |
| 171 | Kasil-1 | 10 | 0.60 | 0 | 0.30 | 0.10 | 25 | 160 | 2 |
| 172 | Kasil-1 | 10 | 0.60 | 0 | 0.30 | 0.08 | 20 | 160 | 2 |
| 173 | UltraSil | 10 | 0.60 | 0 | 0.30 | 0.15 | 20 | 160 | 1 |
| 174 | UltraSil | 10 | 0.60 | 0 | 0.30 | 0.10 | 20 | 160 | 2 |
| 175 | Kasil-1 | 5 | 0.50 | 0 | 0.20 | 0.30 | 30 | 175 | 3 |
| 176 | Kasil-1 | 5 | 0.60 | 0 | 0.20 | 0.30 | 35 | 175 | 3 |
| 177 | Kasil-1 | 5 | 0.51 | 0 | 0.25 | 0.30 | 30 | 175 | 3 |
| 178 | LS-30 | 5 | 0.60 | 0 | 0.20 | 0.30 | 40 | 175 | 3 |
| 179 | UltraSil | 5 | 0.40 | 0 | 0.20 | 0.30 | 30 | 175 | 3 |
| 180 | UltraSil | 10 | 0.60 | 0.25 | 0.30 | 0.20 | 25 | 175 | 3 |

The products were centrifuged, washed three times with deionized water and then subjected to powder X-ray diffraction analysis. The X-ray diffraction patterns showed the products to be pure MCM-68 zeolites.

Example 181

Synthesis of MCM-68

A gel was prepared by adding 5.3 mg deionized water, 121.6 mg Kasil-1 potassium silicate solution (8.3% $K_2O$, 20.8% $SiO_2$), 31.5 mg sodium silicate solution (8.9% $Na_2O$, 28.7% $SiO_2$), 18.2 mg 17.54% KOH solution, 139.6 mg 27.7% 1,1-dimethyl-4-cyclohexylpiperazin-1-ium hydroxide solution, 170.8 mg 15% $Al(NO_3)_3$ solution, 11.1 mg 20% HCl solution, and 1.8 mg MCM-68 seeds to a 1.5 ml stainless steel autoclave. The starting gel had the following molar ratios

| | |
|---|---|
| Si/Al | 5 |
| $OH^-$/Si | 0.2 |
| SDA/Si | 0.3 |
| Alkali metal/Si | 0.6 |
| Na/Total Alkali metal | 0.25 |
| Water/Si | 35 |
| Si from Seeds/Total silica | 0.05 | where SDA is the 1,1-dimethyl-4-cyclohexylpiperazin-1-ium structure directing agent. The mixture was stirred until homogenous and then reacted at autogenous pressure at 160° C. for 3 days in an air oven with tumbling. The product was centrifuged, washed three times with deionized water and then subjected to powder X-ray diffraction analysis. The X-ray diffraction pattern showed the product to be pure MCM-68 zeolite.

EXAMPLES 182 to 193

Further MCM-68 Syntheses

A series of gels were prepared in a manner similar to Example 181 above, but having the molar ratios indicated below, and reacted at the temperature and time indicated. In each case the target (Silica from Seeds)/(Total Silica) ratio was 0.05. In addition, M designates total alkali metal (that is potassium plus any sodium).

| Ex. | Si Source | Si/Al | M/Si | Na/M | OH—/Si | SDA/Si | H₂O/Si | Temp °C. | Time days |
|---|---|---|---|---|---|---|---|---|---|
| 182 | K/Na silicate | 5 | 0.60 | 0.25 | 0.2 | 0.3 | 35 | 160 | 72 |
| 183 | K/Na silicate | 5 | 0.60 | 0.50 | 0.2 | 0.3 | 35 | 160 | 72 |
| 184 | K/Na silicate | 5 | 0.60 | 0.75 | 0.20 | 0.3 | 35 | 160 | 72 |
| 185 | K/Na silicate | 5 | 0.60 | 0.25 | 0.25 | 0.3 | 35 | 160 | 72 |
| 186 | K/Na silicate | 5 | 0.60 | 0.50 | 0.25 | 0.3 | 35 | 160 | 72 |
| 187 | K/Na silicate | 5 | 0.60 | 0.75 | 0.25 | 0.3 | 35 | 160 | 72 |
| 188 | K/Na silicate | 5 | 0.60 | 0.25 | 0.20 | 0.3 | 35 | 175 | 72 |
| 189 | K/Na silicate | 5 | 0.60 | 0.50 | 0.20 | 0.3 | 35 | 175 | 72 |
| 190 | K/Na silicate | 5 | 0.60 | 0.75 | 0.20 | 0.3 | 35 | 175 | 72 |
| 191 | K/Na silicate | 5 | 0.60 | 0.25 | 0.25 | 0.3 | 35 | 175 | 72 |
| 192 | K/Na silicate | 5 | 0.60 | 0.50 | 0.25 | 0.3 | 35 | 175 | 72 |
| 193 | K/Na silicate | 5 | 0.60 | 0.75 | 0.25 | 0.3 | 35 | 175 | 72 |

The products were centrifuged, washed three times with deionized water and then subjected to powder X-ray diffraction analysis. The X-ray diffraction patterns showed the products to be pure MCM-68 zeolites.

Example 194

Synthesis of MCM-68 With 1,1-dimethyl-4-(4-methylcyclohexyl) piperazin-1-ium Hydroxide A gel of stoichiometry:

6SDA-OH:3KNO₃:Al₂O₃:19.3SiO₂:637H₂O where SDA-OH is 1,1-dimethyl-4-(4-methylcyclohexyl)piperazin-1-ium hydroxide (produced in a manner similar to Examples 1 to 6 but starting with 4-methylbromobenzene instead of bromobenzene in Example 1) was prepared by adding 7.9 mg of deionized water, 124.1 mg of DuPont Ludox LS-30 (30.1 wt. % SiO₂), 203.7 mg of a 23.0 wt. % aqueous solution of 1,1-dimethyl-4-(4-methylcyclohexyl) piperazin-1-ium hydroxide, 65.3 mg of 17.5 wt. % solution of KOH, 96.8 mg of a 15 wt. % solution of aluminum nitrate and 2.2 mg of MCM-68 seeds to a stainless steel autoclave. The mixture was stirred until homogenous and then reacted at autogenous pressure at 160° C. for 28 days in an air oven with tumbling. The product was centrifuged, washed three times with deionized water and then subjected to powder X-ray diffraction analysis. The X-ray diffraction pattern showed the product to be pure MCM-68 zeolite.

Example 195

Synthesis of MCM-68 With 1-methyl-1-ethyl-4-(4-methylcyclohexyl) piperazin-1-ium Hydroxide A gel of stoichiometry:

6SDA-OH:3KNO₃:Al₂O₃:19.3SiO₂:637H₂O where SDA-OH is 1-methyl-1-ethyl-4-(4-methylcyclohexyl) piperazin-1-ium hydroxide (produced in a manner similar to Examples 1 to 6 but starting with 4-methylbromobenzene instead of bromobenzene in Example 1 and using iodoethane instead of iodomethane in Example 5) was prepared by adding 0.8 mg of deionized water, 129.5 mg of DuPont Ludox LS-30 (30.1 wt. % SiO₂), mg of a 26.1 wt. % aqueous solution of 1-methyl-1-ethyl-4-(4-methylcyclohexyl) piperazin-1-ium hydroxide, 68.1 mg of 17.5 wt. % solution of KOH, 101.1 mg of a 15 wt. % solution of aluminum nitrate and 2.3 mg of MCM-68 seeds to a stainless steel autoclave. The mixture was stirred until homogenous and then reacted at autogenous pressure at 200° C. for 2 days in an air oven with tumbling. The same mixture was prepared again reacted at autogenous pressure at 160° C. for 7 days. The products were centrifuged, washed three times with deionized water and then subjected to powder X-ray diffraction analysis. The X-ray diffraction patterns showed the products to be pure MCM-68 zeolite.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method of synthesizing a crystalline molecular sieve having an MSE framework type, the method comprising crystallizing a reaction mixture comprising a source of water, a source of an oxide of a tetravalent element, Y, selected from at least one of silicon, tin, titanium, vanadium and germanium, optionally a source of a trivalent element, X, a source of an alkali or alkaline earth metal, M, and a source of organic cations, Q, having the following general structure:

in which $R_1$ is hydrogen or an alkyl group, and $R_2$ and $R_3$ are alkyl groups.

2. The method of claim 1 wherein $R_1$ is a methyl group.

3. The method of claim 1 wherein $R_2$ and $R_3$ are independently selected from methyl and ethyl groups.

4. The method of claim 1 wherein the molar ratio $Q/YO_2$ in said reaction mixture is in the range of from about 0.01 to about 1.0.

5. The method of claim 1 wherein the molar ratio $Q/YO_2$ ratio in said reaction mixture is in the range of from about 0.05 to about 0.7.

6. The method of claim 1 wherein said reaction mixture comprises a source of an oxide of trivalent element, X, selected from at least one of aluminum, boron, gallium, iron and chromium.

7. The method of claim 6 wherein the molar ratio $YO_2/X_2O_3$ in said reaction mixture is in the range of from about 4 to about 200.

8. The method of claim 6 wherein the molar ratio $YO_2/X_2O_3$ in said reaction mixture is in the range of from about 8 to about 120.

9. The method of claim 6 wherein the reaction mixture has the following molar composition:

| | |
|---|---|
| $YO_2/X_2O_3$ | 4 to 200 |
| $H_2O/YO_2$ | 5 to 200 |
| $OH^-/YO_2$ | 0.05 to 1 |
| $M/YO_2$ | 0.05 to 2 |
| $Q/YO_2$ | 0.01 to 1. |

10. The method of claim 6 wherein the reaction mixture has the following molar composition:

| | |
|---|---|
| $YO_2/X_2O_3$ | 8 to 120 |
| $H_2O/YO_2$ | 14 to 50 |
| $OH^-/YO_2$ | 0.10 to 0.53 |
| $M/YO_2$ | 0.15 to 0.9 |
| $Q/YO_2$ | 0.05 to 0.7. |

11. The method of claim 1 wherein said tetravalent element, Y, is silicon.

12. The method of claim 1 wherein said trivalent element, X, is aluminum.

13. The method of claim 1 wherein said alkali or alkaline earth metal, M, comprises at least one of sodium and potassium.

14. The method of claim 1 wherein said alkali or alkaline earth metal, M, is potassium or potassium and sodium such that the molar ratio of Na to the total alkali or alkaline earth metal M is between 0 and about 0.9.

15. The method of claim 1 wherein said reaction mixture comprises seeds of an MSE framework type molecular sieve.

16. The method of claim 15 wherein said seeds are present in an amount such that the molar ratio of seeds/$YO_2$ in said reaction mixture is between about 0.001 and about 0.1.

17. The method of claim 1 wherein the crystallizing is conducted at a temperature between about 100° C. and about 200° C. for up to 28 days.

18. The method of claim 1 wherein the crystallizing is conducted at a temperature between about 145° C. and about 175° C. for about 24 to about 170 hours.

19. A crystalline molecular sieve having an MSE framework type and containing within its pore structure 1,1-dialkyl-4-cyclohexylpiperazin-1-ium cations and/or 1,1-dialkyl-4-alkylcyclohexylpiperazin-1-ium cations.

20. The molecular sieve of claim 19 and having, in its anhydrous, as-synthesized form, an X-ray diffraction pattern including the following lines:

| d (Å) | Relative Intensity $[100 \times I/I(o)]$ |
|---|---|
| 13.56 +/− 0.39 | VW |
| 12.93 +/− 0.37 | M-S |
| 10.92 +/− 0.31 | W |
| 10.16 +/− 0.29 | VW-W |
| 9.15 +/− 0.26 | VW-W |
| 8.19 +/− 0.23 | VW |
| 4.58 +/− 0.13 | W |
| 4.54 +/− 0.13 | W |
| 4.44 +/− 0.12 | W |
| 4.32 +/− 0.12 | VW |
| 4.23 +/− 0.12 | VW |
| 4.10 +/− 0.12 | VS |
| 4.06 +/− 0.12 | M |
| 3.98 +/− 0.11 | W |
| 3.88 +/− 0.11 | M |
| 3.80 +/− 0.11 | VW |
| 3.40 +/− 0.10 | VW |
| 3.24 +/− 0.09 | W |
| 2.90 +/− 0.08 | VW. |

* * * * *